United States Patent [19]

Bauman

[11] 3,953,605

[45] Apr. 27, 1976

[54] ANTIMICROBIAL QUATERNARY AMMONIUM COMPOUNDS COMPOSITIONS

[75] Inventor: Robert Andrew Bauman, New Brunswick, N.J.

[73] Assignee: Colgate-Palmolive Company, New York, N.Y.

[22] Filed: Feb. 20, 1975

[21] Appl. No.: 551,372

Related U.S. Application Data

[62] Division of Ser. No. 242,750, April 10, 1972, Pat. No. 3,882,166.

[52] U.S. Cl. .................................. 424/311; 424/54
[51] Int. Cl.² ............................................ A01N 9/24
[58] Field of Search ................................... 424/311

[56] References Cited
FOREIGN PATENTS OR APPLICATIONS
1,124,508   3/1962   Germany

OTHER PUBLICATIONS

Janata II, Chem. Abs., Vol. 65 (1966), p. 12101.

Caper et al., Chem. Abs., Vol. 72 (1970), 108238j.

*Primary Examiner*—Jerome D. Goldberg
*Assistant Examiner*—Allen J. Robinson
*Attorney, Agent, or Firm*—Herbert S. Sylvester; Murray M. Grill; Robert L. Stone

[57] ABSTRACT

A composition comprising as the active antimicrobial agent, a compound selected from the class of quaternary ammonium compounds which include an aryl ester linked to the quaternary ammonium group by a hydrocarbon chain.

5 Claims, No Drawings

ANTIMICROBIAL QUATERNARY AMMONIUM COMPOUNDS COMPOSITIONS

This application is a division of patent application Ser. No. 242,750 filed Apr. 10, 1972, now U.S. Pat. No. 3,882,166, issued May 6, 1975.

The present invention relates to novel quaternary ammonium compounds represented by the general formula:

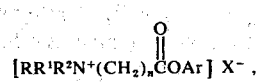

$$[RR^1R^2N^+(CH_2)_n\overset{O}{\underset{\|}{C}}OAr]\ X^-,$$

wherein R is a long chain alkyl group of 12–18 carbon atoms, $R^1$ and $R^2$ are methyl or ethyl groups, n is an integer from 1 to 6, Ar is an aryl radical comprising a phenyl, naphthyl or substituted phenyl or naphthyl wherein said substituents include alkyl, alkoxy, acetamido, amido, phenyl, naphthyl, halo- and/or nitro- radicals, and X is a compatible anion. These quaternary compounds possess superior anti-microbial, anti-caries, and anti-calculus activity, are mild and substantially non-toxic.

Typical examples of the quaternary ammonium compounds embraced by this invention include:
1. 3-(p-cresoxycarbonyl) propyldimethyltetradecylammonium bromide
2. phenoxycarbonylmethyldimethyltetradecylammonium bromide
3. 3-(phenoxycarbonyl)propyldimethyltetradecylammonium bromide
4. 3-(phenoxycarbonyl)propyldimethyldodecylammonium bromide
5. phenoxycarbonylmethyldimethyldodecylammonium bromide
6. p-nitrophenoxycarbonylmethyldimethyltetradecylammonium bromide
7. 3-(p-nitrophenoxycarbonyl)propyldimethyldodecylammonium bromide
8. 3-(p-nitrophenoxycarbonyl)propyldimethyltetradecylammonium bromide
9. 3-(2',4',6' trichlorophenoxycarbonyl)propyldimethyldodecylammonium bromide.
10. 3-(2',4',6' trichlorophenoxycarbonyl)propyldimethyltetradecyl ammonium bromide.
11. 3-(p-cresoxycarbonyl)propyltetradecyldimethyl ammonium chloride.
12. 3-(2',4',6' trichlorophenoxycarbonyl)propyldimethyltetradecyl ammonium iodide.
13. 5-(p-cresoxycarbonyl)pentyldimethylhexadecyl ammonium chloride
14. 6-(phenoxycarbonyl)hexyldiethyloctadecyl ammonium bromide
15. 4-(p-nitrophenoxycarbonyl)butylhexadecyl ammonium bromide
16. 2-naphthyloxycarbonylmethyldimethyltetradecyl ammonium bromide
17. 1-naphthyloxy carbonylmethyldimethyldodecyl ammonium bromide.

The halides, such as the fluorides, the sulfates and methosulfates, and analogous compounds, may also be employed herein as effective antibactericides.

It has been observed that the compounds generally described by the foregoing formula are particularly effective against gram positive organisms such as *Staphylococcus aureus*, *Streptococcus mitis*, *Bacillus subtilis* and *Corynebacterium acnes*.

The anti-microbial nature of the instant novel compounds was shown by a standard test tube serial dilution test in which an appropriate number of test tubes of broth containing decreasing concentrations of the test agent was innoculated with the test organism. The test agent was initially at a 10% concentration in ethanol which was progressively diluted, first tenfold, and then twofold, each time with broth. The broth employed contained 17 gm of trypticase peptone, 3 gm of phytone peptone, 5 gm of sodium chloride, 2.5 gm of dipotassium phosphate, 2.5 gm of dextrose and water to 1 liter. After a suitable period of incubation, the tubes were examined for the presence or absence of growth. The activity of the test agent was the lowest concentration which inhibited the growth of the organism and is expressed as the minimal inhibitory concentration in ug/ml.

TABLE I

| Compound No. | Minimum Inhibitory Concentration (µg/ml) | |
|---|---|---|
| | S. aureus | S. mitis (S-3) |
| 1 | 0.78 | 3.12 |
| 2 | 12.5 | 6.25 |
| 3 | 0.78 | 1.56 |
| 4 | 3.12 | 12.5 |
| 5 | 12.5 | 25 |
| 6 | 6.25 | 12.5 |
| 7 | 6.25 | 25 |
| 8 | 0.78 | 6.25 |
| 9 | 12.5 | 3.12 |
| 10 | 6.25 | 3.12 |

These dilution tests evidence the bacteriostatic effectiveness of compounds of this invention against gram positive bacteria.

When used against bacteria, compounds of the instant invention may be applied directly to the surface to be protected or may be dissolved in a pharmaceutical carrier. Typically, an effective amount, e.g., 0.1 to about 10% by weight of the compound, is included in an inert carrier and a dispersing or surface-active agent. Alternatively, an effective amount, e.g., 0.1 to about 10% by weight, may be incorporated into a solid carrier which may be inert, such as talc, clay, diatomaceous earth, flour, etc.

The quaternary ammonium aryl esters of instant invention are particularly effective in inhibiting the development of dental calculus as shown by the results of tests on litter-mated albino rats, in groups of 15 males and 15 females, who were fed a Zipkin-McClure calculus producing diet. For 6 weeks, the teeth of each animal were swabbed for 30 seconds each day with a 0.1% concentration test solution or water for the control group. The animals were then sacrificed, defleshed, and scored by Baer's method for calculus. The results were analyzed by Student's "t" test and in the results quoted were 99% significant.

TABLE II

| Compound No. | Calculus Reduction |
|---|---|
| 1 | 13.7% |
| 1 | 35.8 |
| 2 | 17.1 |
| 3 | 20.8 |
| 9 | 19.5 |
| 10 | 34.4 |

The results set forth above indicate the significant effectiveness of the quaternary compounds of the invention in inhibiting formation of oral calculus in concentrations as low as 0.1%.

A theoretical explanation for this effectiveness resides in the possible reactivity of the aryl esters with the amino or other group in the protein molecule of plaque to chemically modify plaque and inhibit calculus. The presence of the quaternary ammonium group in aforesaid esters provides substantivity before reaction occurs. More specifically, plaque-reactive compounds have a quaternary ammonium group to provide a temporary binding to the organic constituents of plaque and a reactive site for permanent attachment, whereby the compound is held until the reactive group, namely the aryl ester, has formed a more permanent bond with some atom or group in the protein or carbohydrate of the plaque. Laboratory tests have shown that instant quaternary esters react rapidly with amine groups (i.e., in protein) to form amides, the rate of reaction, however, varying with the particular ester utilized. In addition to the protein breakdown via the amide bond, the quaternary ammonium group may increase the solubility of the plaque, thereby rendering the plaque more dispersible and consequently easily removable from the teeth.

Instant quaternary compounds are also effective in reducing caries, as shown by the results of tests on litter-mated caries-susceptible hamsters, in groups of 15 males and 15 females, who were fed a Mitchell cariogenic diet and received constant deionized water. For 6 weeks, the teeth of each animal were swabbed for 30 seconds each day with a 0.1% concentration test solution or water for the control group. The animals were then sacrificed, defleshed, and scored by a modified version of the Keyes scoring method. Mean averages and percentage changes from the control were determined and tested statistically to determine the significance.

TABLE III

| Compound No. | Caries Reduction | Statistical Significance |
|---|---|---|
| 1 | 52.4% | 99% |
| 2 | 30.6 | — |
| 10 | 49.5 | 95% |

These results are indicative of the significant effectiveness of instant quaternary compounds in the reduction of caries in concentrations as low as 0.1%.

When compounds of the instant invention are intended for use in compositions which reduce formation of caries and inhibit formation of oral calculus, they are typically incorporated in oral preparation in effective amounts up to about 5% by weight, preferably 0.1–1%, and most preferably 0.25–0.5% by weight of the oral preparation. Typically, the oral preparation is a dentifrice, such as a dental cream, tablet or powder, containing as a vehicle about 20–95% by weight of a water-insoluble polishing material, preferably including water-insoluble phosphate such as dicalcium phosphate, tricalcium phosphate, trimagnesium phosphate. The dentifrice may also include water; binders such as glycerine, sorbitol, propylene glycol, and polyethylene glycol 400; detergents; gelling agents such as Irish moss and sodium carboxymethyl cellulose; additional antibacterial agents; coloring or whitening agents; preservatives; silicones; chlorophyl compounds; additional ammoniated materials; flavoring or sweetening materials; and compounds which provide fluorine-containing ion such as sodium fluoride, stannous fluoride and sodium monofluorophosphate.

The oral preparation may also be a liquid such as mouth rinse, which typically contains 20–99% by weight of an aqueous alcohol such as ethanol, n-propyl, or isopropyl alcohol and being present in amount of about 5–30% by weight of the oral preparation.

Such oral preparations are typically applied by brushing the teeth or rinsing the oral cavity for 30–90 seconds at least once daily. Typical oral preparations of the invention which can be applied in this manner are set forth below.

EXAMPLE 1

| Dental Cream | % |
|---|---|
| 3-(p-cresoxycarbonyl)propyldimethyltetra-decylammonium bromide | 0.50 |
| Nonionic detergent* | 1.00 |
| Glycerine | 22.00 |
| Sodium pyrophosphate | 0.25 |
| Carboxymethyl cellulose | 0.85 |
| Sodium saccharin | 0.20 |
| Sodium benzoate | 0.50 |
| Calcium carbonate (precipitated) | 5.00 |
| Dicalcium phosphate dihydrate | 46.75 |
| Flavor | 0.80 |
| Water | 22.15 |

*Tween 80 - Polyoxyethylene (20 moles ethylene oxide) sorbitan monooleate.

EXAMPLE 2

| Mouthwash | % |
|---|---|
| Compound No. 1 | 0.25 |
| Nonionic detergent (Pluronic F-68)* | 1.00 |
| Ethyl alcohol (containing flavor) | 15.00 |
| Glycerine | 10.00 |
| Saccharin | 0.02 |
| Water | 73.73 |

*Block polymer of 80% polyoxyethylene and 20% polyoxypropylene.

In lieu of Compound No. 1, any of the listed 17 quaternary compounds and analagous compounds may be incorporated into above or similar dentifrice or mouth rinse formulations to provide protection against plaque formation, calculus and/or caries.

Instant quaternary ammonium arylesters can be prepared by a two-step process of reacting essentially equimolar quantities of a phenol or naphthol with a holo-alkanoic acid, or salt of a phenol or naphthol with a halo-alkanoyl halide to form an aryl halo-alkanoate; followed by reacting with essentially an equimolar amount of a tertiary amine to form the quaternary ammonium salt, as illustrated by the following equations:

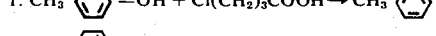

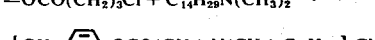

A salt of a phenol may be used in lieu of the phenol in Step 1, as shown below:

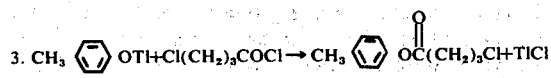

3. $CH_3\langle\bigcirc\rangle OTl+Cl(CH_2)_3COCl \rightarrow CH_3\langle\bigcirc\rangle OC(CH_2)_3Cl+TlCl$ The phenol salt may be obtained by the reaction illustrated by the following equation:

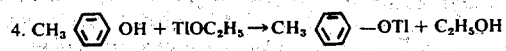

4. $CH_3\langle\bigcirc\rangle OH + TlOC_2H_5 \rightarrow CH_3\langle\bigcirc\rangle -OTl + C_2H_5OH$ Other phenolic salts may be used in lieu of thallous phenolate, inclusive of the alkali metal phenolic salts, etc. as the reactant with a halo-alkanoyl halide in accordance with Equation 3. The preferred process utilizes the phenol or naphthol reactant as illustrated by Equation 1.

with stirring 120 g (0.40 mol) of thallous phenoxide. After standing overnight, the reaction mixture was filtered from thallous bromide, washed with water until neutral, and then dried over Drierite. After removal of the ether, the phenyl bromoacetate was distilled through a short Vigreux column and product was collected from 80°–86° (1.3 T).

A mixture of 55 g (0.26 mol) phenyl bromoacetate and 62 g (0.26 mol) of tetradecyldimethylamine was allowed to stand at room temperature for three days. The resultant crystalline mass was washed well with ether and dried to 114 g. Recrystallized from ethyl acetate and vacuum dried, the compound melted at 87°–91.5°.

Analysis: Calculated for $C_{24}H_{42}BrNO_2$: C, 63.14; H, 9.27; Br, 17.50. Found: C, 62.88; H, 9.14; Br, 17.61.

EXAMPLE 4

Other compounds prepared in accordance with the procedure of Example 3 include:

| | | M.P. | % Br Calcd. | Found |
|---|---|---|---|---|
| 1. | $[CH_3\langle\bigcirc\rangle OCO(CH_2)_3N(CH_3)_2C_{14}H_{29}]$ Br | 104–108° | 16.03 | 15.98 |
| 3. | $[\langle\bigcirc\rangle OCO(CH_2)_3N(CH_3)_2C_{14}H_{29}]$ Br | 89–92.5° | 16.49 | 16.42 |
| 4. | $[\langle\bigcirc\rangle OCO(CH_2)_3N(CH_3)_2C_{12}H_{25}]$ Br | 84–89.5° | 17.50 | 17.48 |
| 5. | $[\langle\bigcirc\rangle OCOCH_2N(CH_3)_2C_{12}H_{25}]$ Br | 76–81° | 18.65 | 18.63 |
| 6. | $[NO_2\langle\bigcirc\rangle OCOCH_2N(CH_3)_2C_{14}H_{29}]$ Br | 119–120° | 15.93 | 15.86 |
| 7. | $[NO_2\langle\bigcirc\rangle OCO(CH_2)_3N(CH_3)_2C_{12}H_{25}]$ Br | | 15.93 | 15.84 |
| 8. | $[NO_2\langle\bigcirc\rangle OCO(CH_2)_3N(CH_3)_2C_{14}H_{29}]$ Br | 120–2° | 15.09 | 15.08 |
| 9. | $[Cl\langle\bigcirc\rangle^{Cl}_{Cl} OCO(CH_2)_3N(CH_3)_2C_{12}H_{25}]$ Br | 139–146° | 14.23 | 14.25 |
| 10. | $[Cl\langle\bigcirc\rangle^{Cl}_{Cl} OCO(CH_2)_3N(CH_3)_2C_{14}H_{29}]$ Br | 152–5° | 13.59 | 13.84 |

The following examples illustrate the manner in which compounds of this invention are prepared.

EXAMPLE 3

Preparation of phenoxycarbonylmethyltetradecyldimethyl ammonium bromide:

Compound 2. $[\langle\bigcirc\rangle OCOCH_2N(CH_3)_2C_{14}H_{29}]$ Br

To a solution of 37.6 g (0.40 mol) phenol in 600 ml of ether was added with stirring 100 g (0.40 mol) of thallous ethoxide. The white precipitate of 120 g thallous phenoxide was removed by filtration and dried in vacuum. To a solution of 80.9 g (0.40 mol) bromoacetyl bromide in one liter of ether was added portionwise

EXAMPLE 5

Preparation of 3-(p-cresoxycarbonyl)propyltetradecyldimethyl ammonium chloride:

Compound 11: $[CH_3\langle\bigcirc\rangle -OCO(CH_2)_3N(CH_3)_2C_{14}H_{29}]$ Cl In a 2 liter one-neck flask fitted with a Dean-Stark trap and a reflux condenser were placed 84.7 g (0.78 mol) p-cresol, 87.4 g (0.71 mol) 4-chlorobutyric acid, 875 ml toluene, and 1 ml concentrated sulfuric acid. The mixture was refluxed for three days. After neutralizing the acid with 6 g of sodium bicarbonate, the reaction mixture was filtered, and the solvent removed by vacuum evaporation. The residue was distilled through a 15 inch Vigreux column to yield 106 g of colorless oil boiling at 144° (4T), and confirmed by infrared and nmr spectra as p-cresyl 4-chlorobutyrate.

A mixture of 89.5 g (0.42 mol) p-cresyl 4-chlorobutyrate and 102.0 g (0.42 mol) tetradecyldimethylamine was prepared in a 500 ml Erlenmeyer flask, stoppered and placed in an oven at 100° for 3 days. After cooling to room temperature, the crystalline mass was slurried with ether, filtered, and dried to 145 g. The product was recrystallized from ethyl acetate; m.p. 110°–114° to a liquid crystal, 166°–167° to a clear liquid.

Analysis: Calculated for $C_{27}H_{48}ClNO_2$: C, 71.41; H, 10.65; Cl, 7.81. Found: C, 71.43; H, 10.78; Cl, 7.83.

Although this invention has been described with reference to specific examples, it will be apparent to one skilled in the art that various modifications may be made thereto which fall within its scope.

What is claimed:

1. An antimicrobial composition comprising about 0.1–10% by weight of an antimicrobial agent having the structural formula:

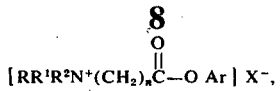

wherein R is a long chain alkyl group of 12–18 carbon atoms; $R^1$ and $R^2$ are methyl or ethyl groups; $n$ is an integer from 1 to 6; Ar is a substituted aryl radical selected from the group consisting of phenyl and naphthyl, said substituted moiety being selected from the group consisting of tri-halo-and mono-nitro-radicals; and X is an anion selected from the class consisting of halides, sulfates and methosulfates, and a pharmaceutical carrier therefor.

2. The antimicrobial composition as set forth in claim 1 wherein X is an halide.

3. The antimicrobial composition as set forth in claim 1 wherein said agent is 3-(2',4',6' trichlorophenoxycarbonyl)propyldimethyltetradecyl ammonium halide.

4. The antimicrobial composition claimed in claim 1 wherein said agent is p-nitrophenoxycarbonylmethyldimethyltetradecylammonium bromide.

5. The antimicrobial composition claimed in claim 1 wherein said agent is 3-(p-nitrophenoxycarbonyl) propyldimethyltetradecylammonium bromide.

* * * * *